(12) United States Patent
Dai et al.

(10) Patent No.: US 10,207,107 B2
(45) Date of Patent: Feb. 19, 2019

(54) ELECTROSTIMULATION APPARATUS

(71) Applicants: Quanqin Dai, Diamond Bar, CA (US); Pu Jiang, Shenzhen (CN)

(72) Inventors: Quanqin Dai, Diamond Bar, CA (US); Pu Jiang, Shenzhen (CN)

( * ) Notice: Subject to any disclaimer, the term of this patent is extended or adjusted under 35 U.S.C. 154(b) by 0 days.

(21) Appl. No.: 15/269,846

(22) Filed: Sep. 19, 2016

(65) Prior Publication Data

US 2017/0216592 A1 Aug. 3, 2017

(30) Foreign Application Priority Data

Jan. 28, 2016 (CN) ..................... 2016 2 0087122 U
Mar. 4, 2016 (CN) ..................... 2016 2 0168442 U (51) Int. Cl.
*A61N 1/36* (2006.01)
*A61N 1/04* (2006.01)
*A61F 7/00* (2006.01)
*A61F 7/02* (2006.01)

(52) U.S. Cl.
CPC .......... *A61N 1/36014* (2013.01); *A61F 7/007* (2013.01); *A61F 7/02* (2013.01); *A61N 1/0484* (2013.01); *A61N 1/0492* (2013.01); *A61F 2007/0096* (2013.01); *A61F 2007/0228* (2013.01); *A61F 2007/0233* (2013.01); *A61F 2007/0234* (2013.01); *A61F 2007/0236* (2013.01)

(58) Field of Classification Search
CPC ........................ A61F 7/007; A61F 7/02; A61F 2007/0001–2007/0045; A61F 2007/007; A61N 1/04–1/0492
See application file for complete search history.

(56) References Cited

U.S. PATENT DOCUMENTS

2007/0142891 A1* 6/2007 Stanley ................... A61F 7/007
607/144
2013/0238042 A1* 9/2013 Gildersleeve ......... A61F 7/0085
607/3
2016/0129274 A1* 5/2016 Park ...................... A61N 2/002
600/14

* cited by examiner

*Primary Examiner* — Scott M. Getzow
(74) *Attorney, Agent, or Firm* — Che-Yang Chen; Law Offices of Scott Warmuth (57) ABSTRACT

An electrostimulation apparatus may comprise a control unit, a power supply and a carrier separated or combined. The control unit is configured to provide the electrical current to an electrode layer settled on or inside the carrier, and the power supply is configured to heat a heating piece settled on or inside the carrier. The carrier has a plurality of connecting portions which are configured to electrically connect to the control unit, the power supply, the heating piece and the electrode layer. Furthermore, the electrode layer is electrically connected to the control unit through the connecting portions, and also the heating piece is electrically connected to the power supply through the connecting portions. Also, the heating piece and the electrode layer are attached on the carrier, and the carrier can be used to serve both training and treatment purposes for a user.

10 Claims, 8 Drawing Sheets

ELECTROSTIMULATION APPARATUS

FIELD OF THE INVENTION

The present invention relates to an electrostimulation apparatus, and more particularly to an electrostimulation apparatus capable of providing electrical current and heat simultaneously, electrical current only, and heat only for therapeutic or training purpose. In addition, the control unit of the electrostimulation apparatus may be used as a thermometer to measure temperature.

BACKGROUND OF THE INVENTION

Currently, transcutaneous electrical nerve stimulation (TENS) apparatus and electrical muscle stimulation (EMS) apparatus are two main electrostimulation apparatuses in the market which are used of electric impulses produced by a device to relieve pain or stimulate muscle. The electrostimulation apparatus always has at least two conductive electrodes which are electrically connected to a control unit and adhere to user's skin. Then, through operating the control unit, the electrodes are configured to provide different frequencies of impulses thus achieving therapeutic or training purpose.

However, the conventional electrostimulation apparatus has following disadvantages: the apparatus can only provide impulses to user and without heating function, the efficiency of the therapy or training may be greatly reduced. For now, the electrostimulation apparatus such as TENS and EMS is usually cooperatively used with a heating accessory, and the control unit thereof has several buttons and has at least two wires to electrically and respectively connect to the electrode and the heating accessory thus achieving operation. Nevertheless, the heating accessory is usually heavy and since the electrode and the heating accessory is separated, it is hard and inconvenient to provide impulses and heating to the same part of user simultaneously. Therefore, there remains a need for a new and improved design for an electrostimulation apparatus to overcome the problems presented above.

SUMMARY OF THE INVENTION

The present invention provides an electrostimulation apparatus which comprises a control unit, a power supply and a carrier. The control unit is configured to provide the electrical current to an electrode layer on or inside the carrier, and the power supply is configured to heat a heating piece settled on or inside the carrier. The carrier has a plurality of connecting portions which are configured to electrically connect to the control unit, the power supply, the heating piece and the electrode layer. Furthermore, the electrode layer is electrically connected to the control unit through the connecting portions, and also the heating piece is electrically connected to the power supply through the connecting portions. Also, the heating piece and the electrode layer are separately attached on the carrier, and the carrier can be used to serve both training and treatment purposes for a user.

In one embodiment, the heating piece and the electrode layer are parallel and sequentially attached on the carrier, and an insulating layer is settled between the heating piece and the electrode layer thus preventing the electrical current from conducting therebetween. Wherein the insulating layer formed in an O-shaped or alternative shape is made of a heat-resisting material, and the heating piece is formed in a C-shaped or alternative shapes.

In another embodiment, the control unit is optionally configured to have a communicate module settled therein. Through the communicate module, the control unit is configured to connect to a mobile terminal or a wireless remote controller thus achieving remote operation. Wherein the communicate module can be an APP installed in a smart phone or other networking devices, and the wireless linking technology can be Bluetooth, radio, infrared date association (IRDA) or WIFI. Also, the control unit may be used to measure the temperature on the carrier and/or the user.

In still another embodiment, the electrode layer is respectively and electrically connected to the corresponding connecting portions, and the heating piece is electrically connected to the power supply through the connecting portions and is configured to heat the heating piece. Wherein the electrode layer comprises a number of electric conductors such as conductive fabric which are insulated from each other and are respectively and electrically connected to the corresponding connecting portions. Also, the electric conductors are formed in arc shape or alternative shapes.

In a further embodiment, a tensile spacer is optionally formed between each of the connecting portions and the carrier. Since the carrier is made of soft material which has weak mechanical strength, the spacer is configured to improve stability and prevent the connecting portions from detaching from the carrier when pulled. Also, the carrier has a fixing feature or unit (such as a strap or a velcro) to secure the carrier on a portion of a user's body.

In still a further embodiment, the connecting portion can be a conductive snap fastener, a conductive pin or other preferable connectors. A surface of the control unit has a connecting unit which is configured to connect to the connecting portions through wires or cordless/wireless method. Also, the surface of the control unit also comprises a plurality of buttons which are configured to control the operations such as the frequency of impulses. The power supply is configured to connect to the connecting portions through wires or cordless/wireless method. Wherein the power supply can be a power adapter, a portable power supply, a vehicle power supply or other power supplies. The connecting portion is connected to the control unit or the power supply through a magnetic set, a set of conductive snap fastener, a flexible glue set, a pin-socket set, or other preferable sets. The control unit, power supply, and carrier could be of three separate units, two combined units, or one combined unit.

In yet a further embodiment, the carrier is a belt, a bandage, a wrap/sleeve, a guard, a pad, a grove, a sock, a shoe, a sole, shorts, pants, shirts, clothes, or other products.

Comparing with conventional electrostimulation apparatus, the present invention is advantageous because: through settling the heating piece and the electrode layer on the carrier, the electrostimulation apparatus in the present invention is configured to provide electrical current and heat simultaneously, electrical current only, and heat only to a designated part of a user, which is convenient to use and enhances therapeutic or training effect.

DETAILED DESCRIPTION OF THE INVENTION

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications that might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

Figure 1:
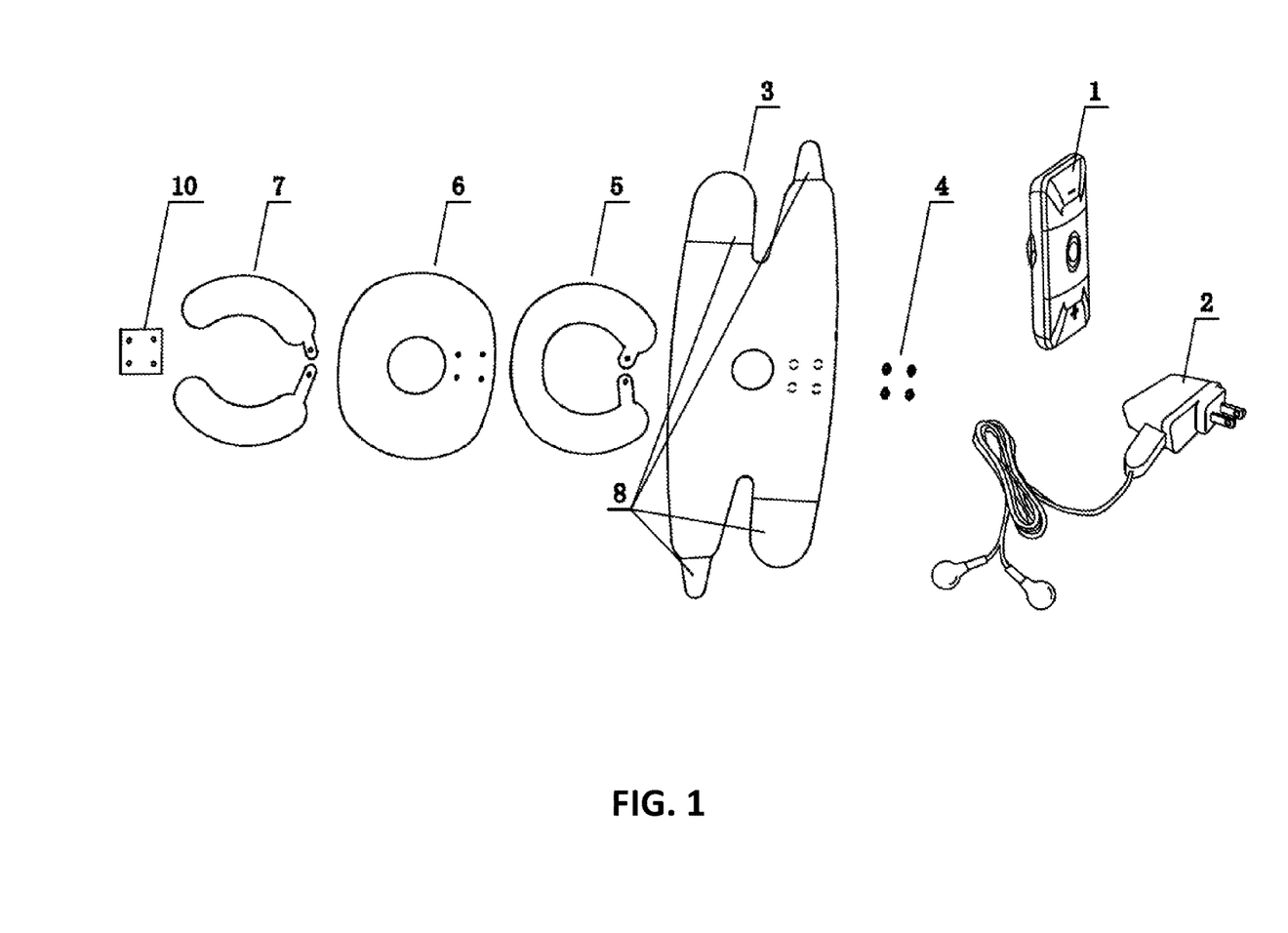
FIG. 1 is an exploded view of an electrostimulation apparatus in the present invention.

In order to further understand the goal, characteristics and effect of the present invention, a number of embodiments along with the drawings are illustrated as following:

Referring to FIG. 1, the present invention provides an electrostimulation apparatus which comprises a control unit (1), a power supply (2) and a carrier (3). The control unit (1) is configured to provide the electrical current to an electrode layer (7), and the power supply (2) is configured to heat a heating piece (5) settled on or inside the carrier (3). The carrier (3) has a plurality of connecting portions (4) which are configured to electrically connect to the control unit (1), the power supply (2), the heating piece (5) and the electrode layer (7). Furthermore, the electrode layer (7) is electrically connected to the control unit (1) through the connecting portions (4), and also the heating piece (5) is electrically connected to the power supply (2) through the connecting portions (4). Also, the heating piece (5) and the electrode layer (7) are separately attached on the carrier (3), and the carrier (3) can be used to serve both training and treatment purposes for a user.

Moreover, the heating piece (5) and the electrode layer (7) are parallel and sequentially attached on the carrier (3), and an insulating layer (6) is settled between the heating piece (5) and the electrode layer (7) thus preventing the electrical current from conducting therebetween. Wherein the insulating layer (6) formed in an O-shaped or alternative shape is made of a heat-resisting material, and the heating piece (5) is formed in a C-shaped or alternative shapes.

In addition, the control unit (1) is optionally configured to have a communicate module settled therein. Through the communicate module, the control unit is configured to connect to a mobile terminal or a wireless remote controller thus achieving remote operation. Wherein the communicate module can be an APP installed in a smart phone or other networking devices, and the wireless linking technology can be Bluetooth, radio, infrared date association (IRDA) or WIFI. Also, the control unit may be used to measure the temperature on the carrier and/or the user.

Furthermore, the electrode layer (7) is respectively and electrically connected to the corresponding connecting portions (4), and the heating piece (5) is electrically connected to the power supply (2) through the connecting portions (4). Wherein the electrode layer (7) comprises a number of electric conductors such as conductive fabric which are insulated from each other and are respectively and electrically connected to the corresponding connecting portions (4). Also, the electric conductors are formed in arc shape or alternative shapes.

Additionally, a tensile spacer (10) is optionally formed between each of the connecting portions (4) and the carrier (3). Since the carrier (3) is made of soft material which has weak mechanical strength, the spacer (10) is configured to improve stability and prevent the connecting portions (4) from detaching from the carrier (3) when pulled. Also, the carrier (3) has a fixing unit (8) (such as a strap or a velcro) to secure the carrier (3) on a portion of a user's body. In one embodiment, the carrier (3) is a knee wrap.

Further, the connecting portion can be a conductive snap fastener, a conductive pin or other preferable connectors. A surface of the control unit (1) has a connecting unit which is configured to connect to the connecting portions (4) through wires or cordless/wireless method. Also, the surface of the control unit (1) also comprises a plurality of buttons which are configured to control the operations such as the frequency of impulses. The power supply (2) is configured to connect to the connecting portions (4) through wires or cordless/wireless method. Wherein the power supply (2) can be a power adapter, a portable power supply, a vehicle power supply or other power supplies. The connecting portion (4) is connected to the control unit (1) or the power supply (2) through a magnetic set, a set of conductive snap fastener, a flexible glue set, a pin-socket set, or other preferable sets. The control unit (1) and the power supply (2) could be of two separate units or one combined unit.

Figure 2:
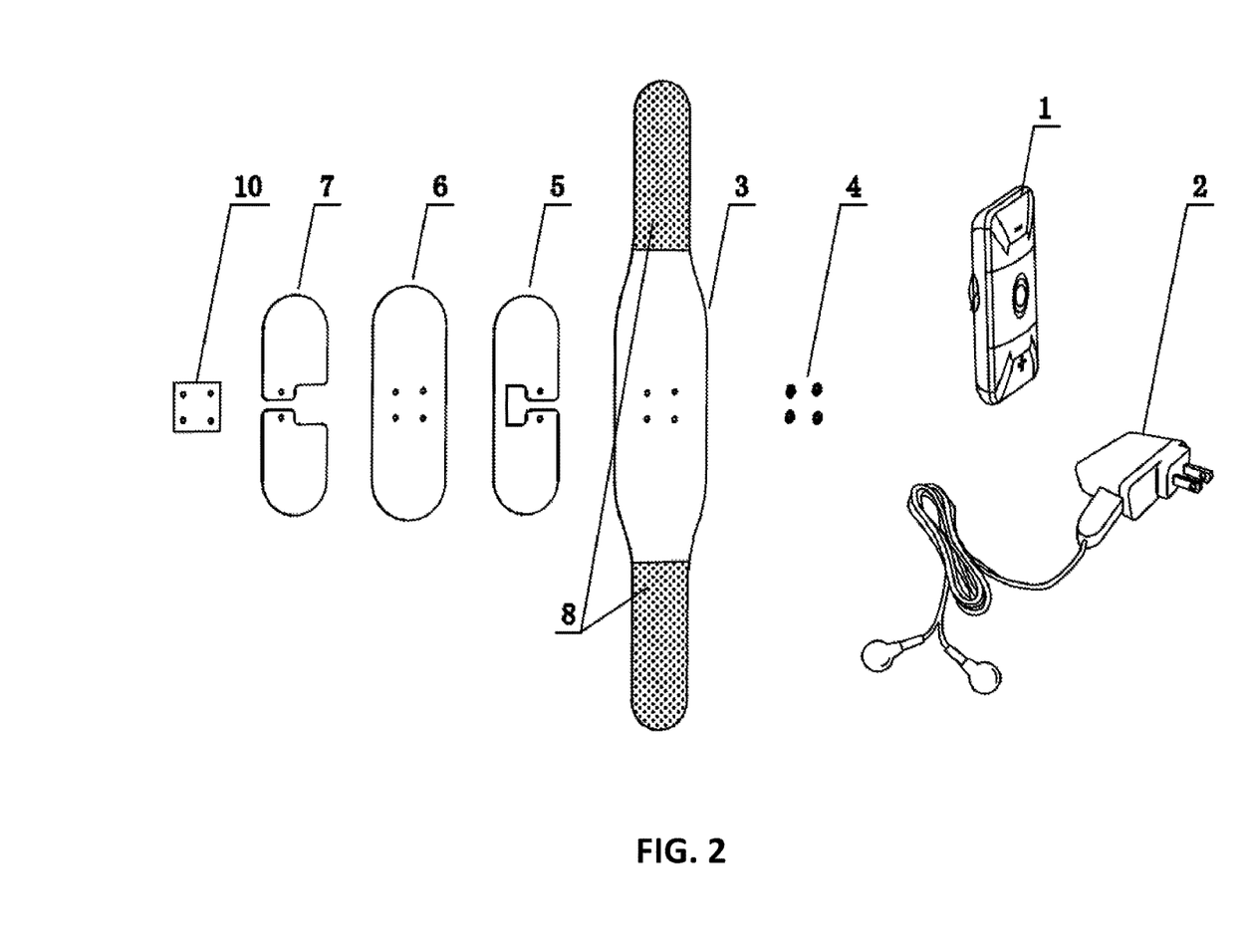
FIG. 2 is an exploded view of the second embodiment of the electrostimulation apparatus in the present invention.

In another embodiment, referring to FIG. 2, the carrier (3) is a bandage, and the heating piece is formed in a C-shaped. Also, the insulating layer (6) is a plate formed in oval shape, and the electric conductors of the electrode layer (7) are formed in semi-elliptic shape.

Figure 3:
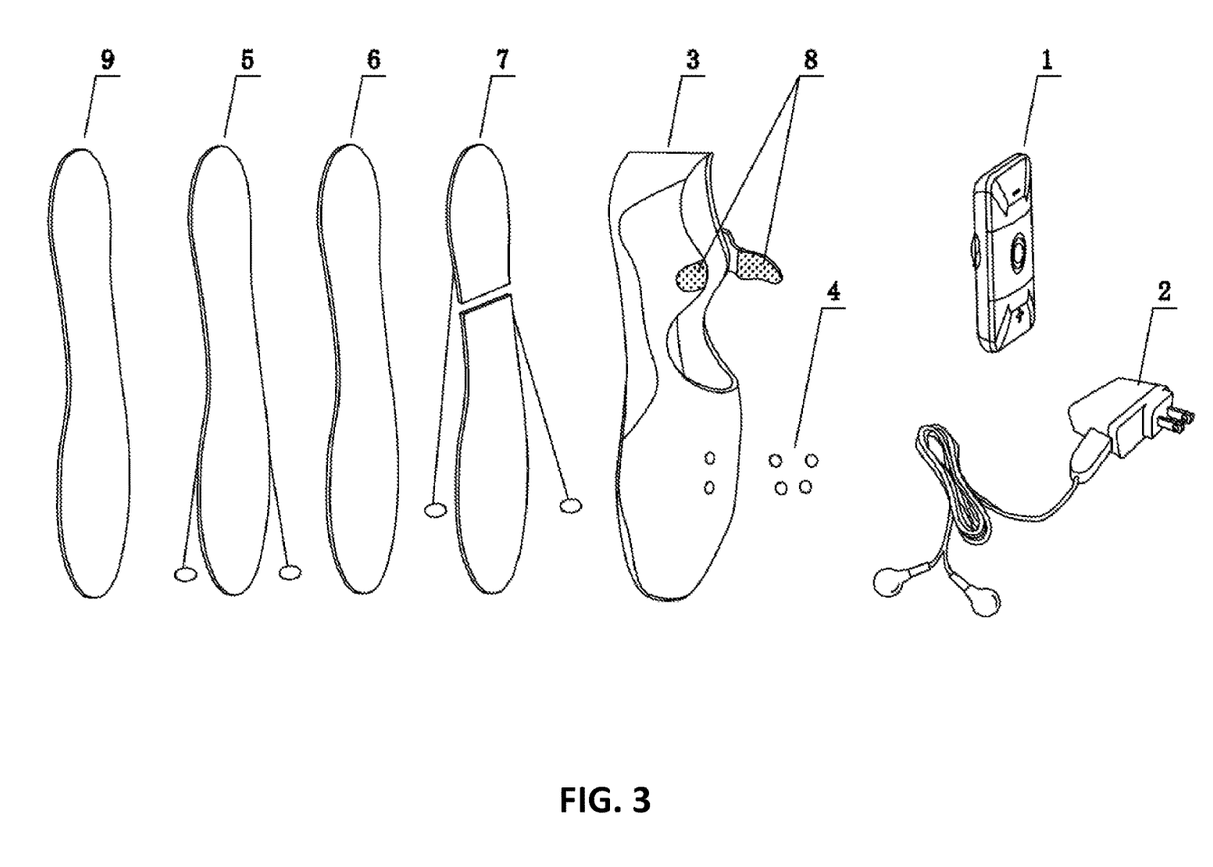
FIG. 3 is an exploded view of the third embodiment of the electrostimulation apparatus in the present invention.

In still another embodiment, referring to FIG. 3, the carrier (3) is a pair of shoes, and each of shoe has the heating piece (5), the insulating layer (6) and the electrode layer (7) which are formed in insole shape, and each of sizes of the heating piece (5), the insulating layer (6) and the electrode layer (7) is adjustable and customized to fit different sizes of the carrier (3). Also, the carrier (3) is attached with a sole (9) to settle the components therebetween.

Figure 4:
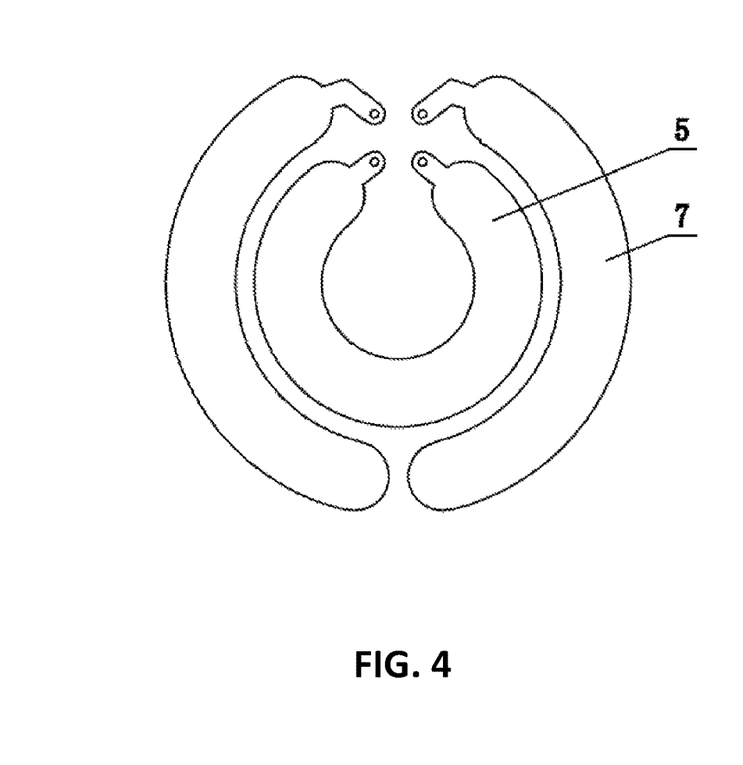
FIG. 4 is a schematic view of the fourth embodiment illustrating an arrangement of a heating piece and an electrode layer of the electrostimulation apparatus in the present invention.

In a further embodiment, referring to FIG. 4, the heating piece (5) and the electrode layer (7) is secured on the carrier (3) in a circle pattern, the heating piece (5) formed in a C-shaped is located at an internal of the circle, and the electric conductors of the electrode layer (7) formed in arc shape are located around an outer periphery of the heating piece (5).

Figure 5:
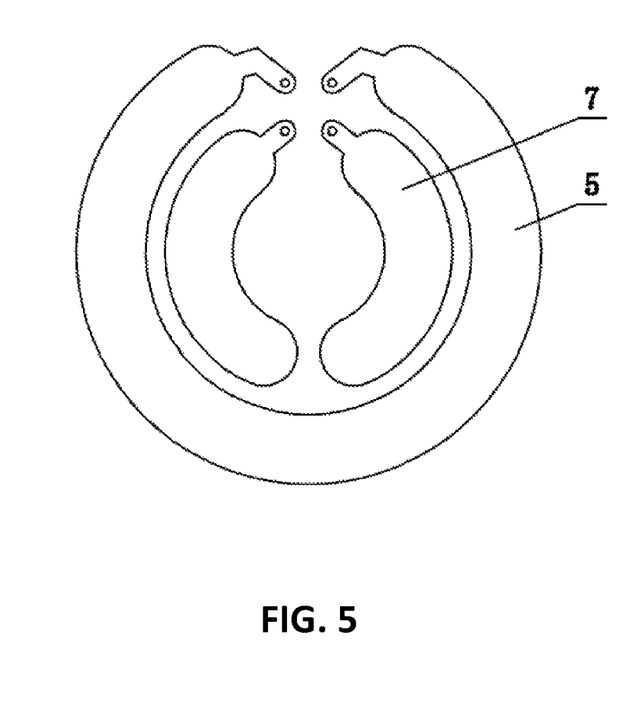
FIG. 5 is a schematic view of the fifth embodiment illustrating an arrangement of the heating piece and the electrode layer of the electrostimulation apparatus in the present invention.

In still a further embodiment, referring to FIG. 5, the heating piece (5) and the electrode layer (7) is secured on the carrier (3) in a circle pattern, the electric conductors of the electrode layer (7) formed in arc shape are located at an internal of the circle, and the heating piece (5) formed in a C-shaped is located around an outer periphery of the two electric conductors.

Figure 6:
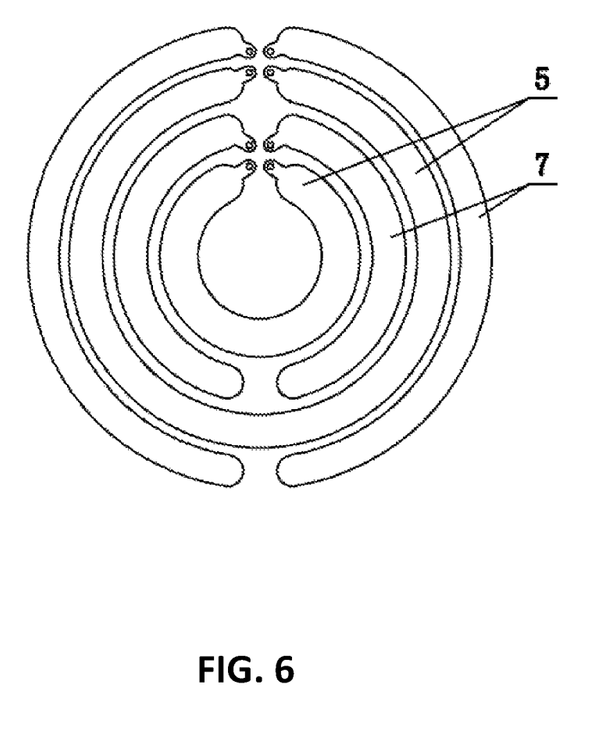
FIG. 6 is a schematic view of the sixth embodiment illustrating an arrangement of the heating piece and the electrode layer of the electrostimulation apparatus in the present invention.

In yet a further embodiment, referring to FIG. 6, the electrostimulation apparatus has two sets of the heating pieces (5) and the electrode layers (7) which are secured on the carrier (3) and alternatively arranged in a circle pattern. Namely, the heating piece (5) formed in a C-shaped is located at an internal of the circle, and the electrode layer (7) are located around an outer periphery of the heating piece (5) in sequence. Wherein the two electric conductors of the electrode layer (7) formed in arc shape.

Figure 7:
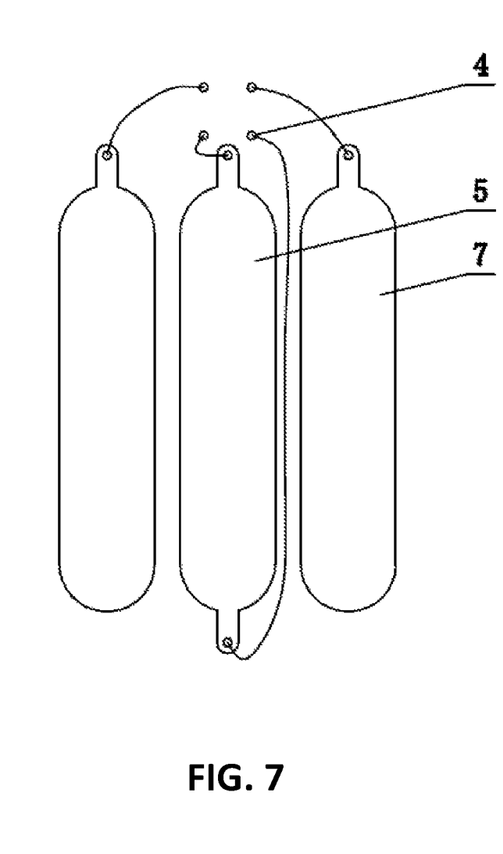
FIG. 7 is a schematic view of the seventh embodiment illustrating an arrangement of the heating piece and the electrode layer of the electrostimulation apparatus in the present invention.

In a particular embodiment, the heating piece (5) and the electric conductors of the electrode layer (7) are secured on the carrier (3) side by side as shown in FIG. 7.

Figure 8:
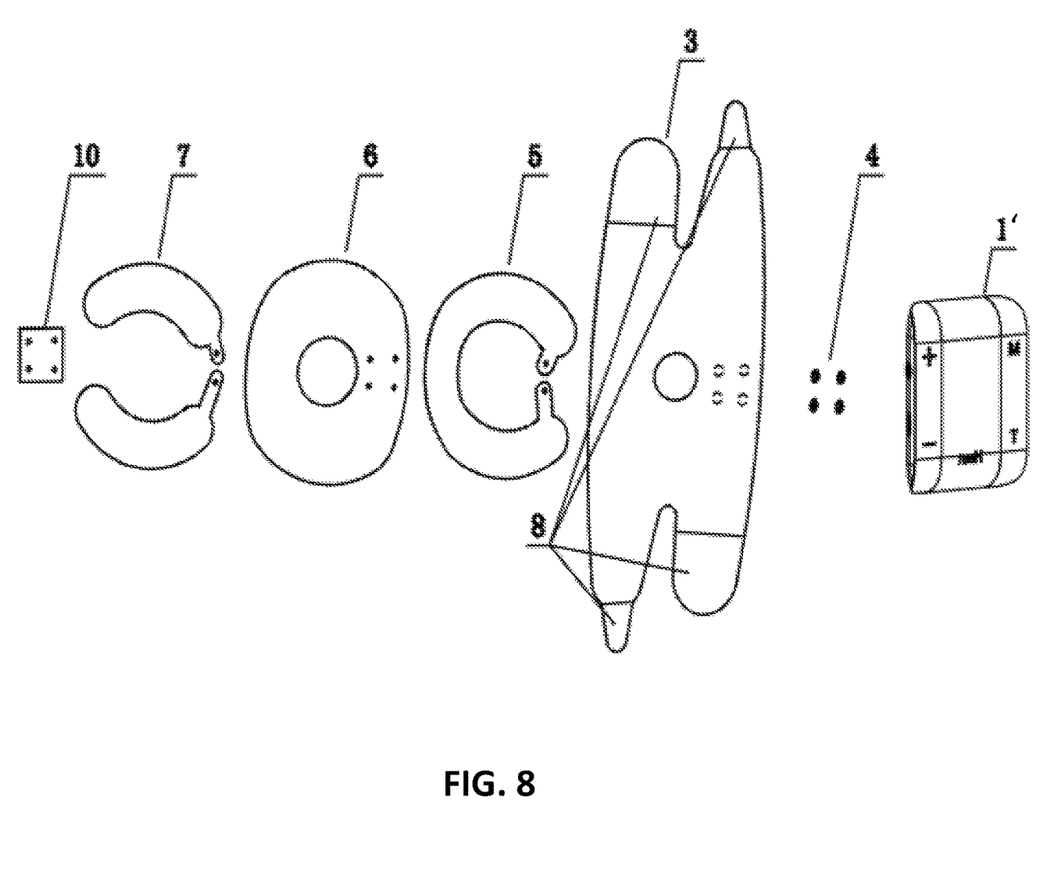
FIG. 8 is an exploded view of the eighth embodiment of the electrostimulation apparatus in the present invention, where the control unit and the power supply are combined and connected to the carrier cordlessly.
Figure 9:
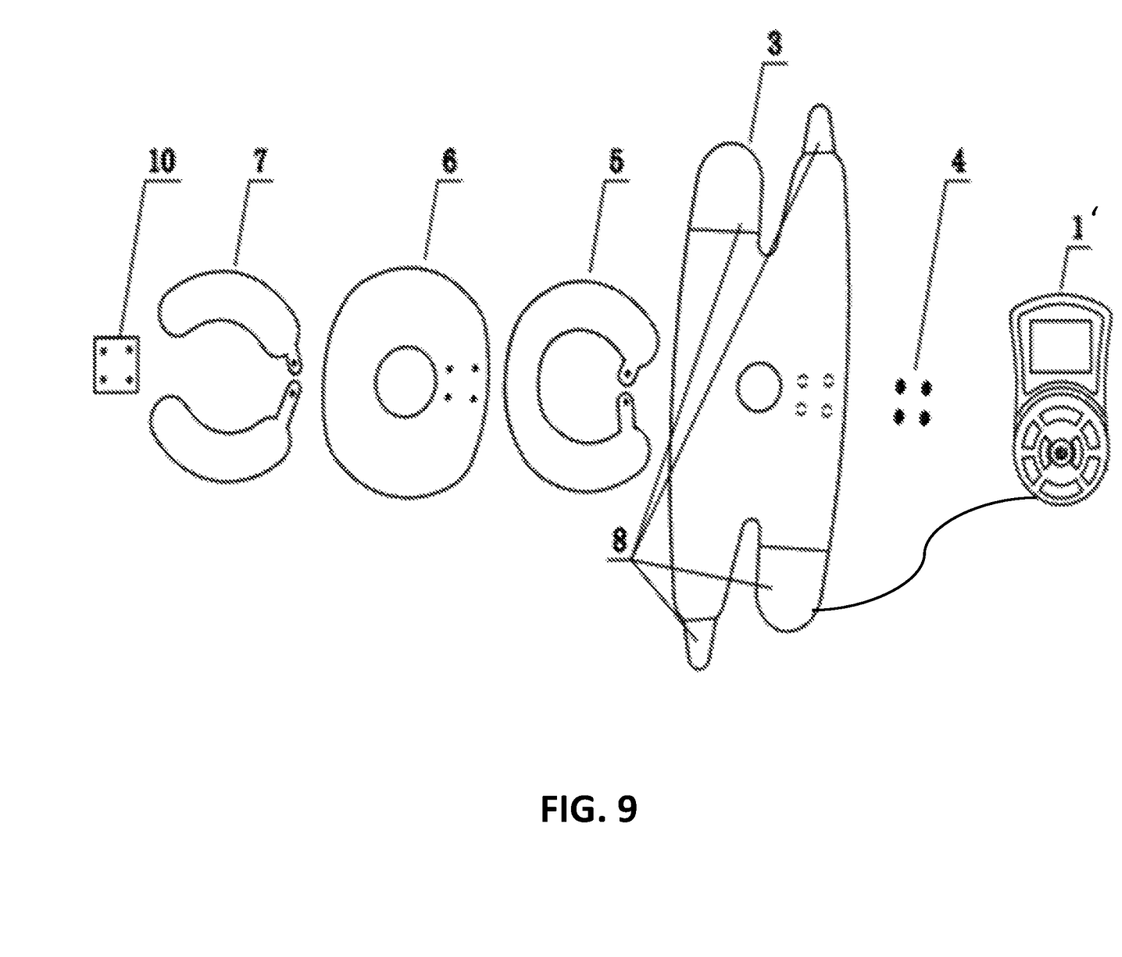
FIG. 9 is an exploded view of the ninth embodiment of the electrostimulation apparatus in the present invention, where the control unit and the power supply are combined and connected to the carrier through wires.
Figure 10:
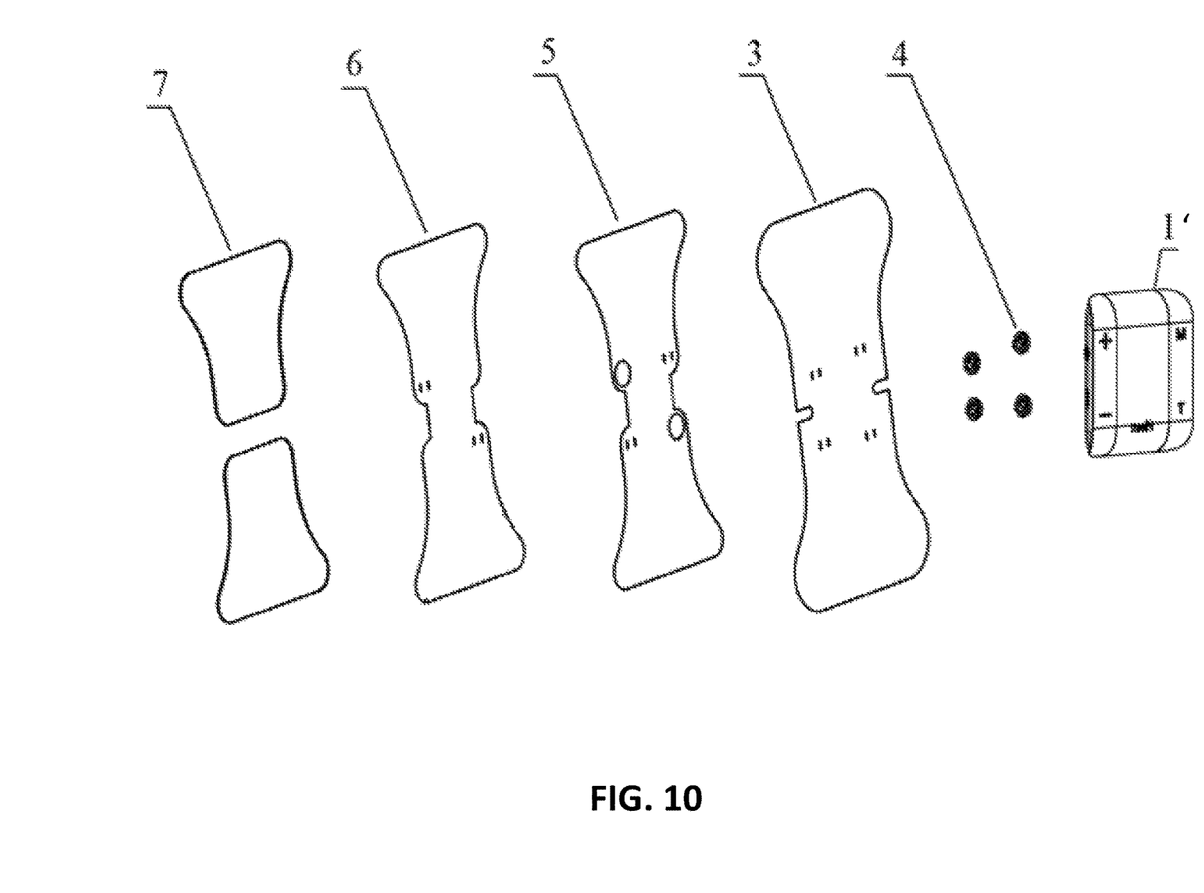
FIG. 10 is an exploded view of the tenth embodiment of the electrostimulation apparatus in the present invention, where the control unit and the power supply are combined and connect to the carrier cordlessly.

In an alternative embodiment, a control unit (1') is the combination of the control unit (1) and the power supply (2). It is noted that the control unit (1') can be cordlessly connected to the carrier (3) as shown in FIG. 8, whereas the control unit (1') in FIG. 9 is connected to the carrier (3) through wires. In still an alternative embodiment for the electrostimulation apparatus with a different shape, the control unit (1') is also configured to cordlessly connect to the carrier (3) as shown in FIG. 10.

Comparing with conventional electrostimulation apparatus, the present invention is advantageous because: through settling the heating piece (5) and the electrode layer (7) on the carrier (3), the electrostimulation apparatus in the present invention is configured to provide electrical current and heat simultaneously, electrical current only, and heat only to a designated part of a user, which is convenient to use and enhances therapeutic or training effect.

Having described the invention by the description and illustrations above, it should be understood that these are exemplary of the invention and are not to be considered as limiting. Accordingly, the invention is not to be considered as limited by the foregoing description, but includes any equivalents.

What is claimed is:

1. An electrostimulation apparatus comprising:
   a control unit configured to provide electrical current to a substantially circular electrode layer settled on or inside a carrier;
   a power supply configured to heat a substantially circular heating piece corresponding to a shape of the electrode layer settled on or inside the carrier; and
   the carrier having a plurality of connecting portions which are configured to electrically connect between the control unit and the electrode layer and between the power supply and the circular heating piece; the control unit, power supply, and carrier are configured to be of three separate units, two combined units, or one combined unit,
   wherein the heating piece and the electrode layer are secured on or inside the carrier in a stack or alternative pattern, and a substantially circular insulating layer secured on or inside the carrier is located therebetween.

2. The electrostimulation apparatus of claim 1, wherein the heating piece and the electrode layer are secured on or inside the carrier in a stack, overlap, parallel, circle, or alternative pattern.

3. The electrostimulation apparatus of claim 2, wherein the insulating layer is made of heat-resisting materials.

4. The electrostimulation apparatus of claim 1, wherein one or more sets of the heating pieces and the electrode layers are secured on or inside the carrier in a stack, overlap, parallel, circle, or alternative pattern.

5. The electrostimulation apparatus of claim 1, wherein the control unit has a communicate module settled therein, and through the communicate module, the control unit is configured to connect to a mobile terminal or a wireless remote controller thereby achieving remote operation.

6. The electrostimulation apparatus of claim 5, wherein the electrodes are respectively and electrically connected to corresponding connecting portions, and the electrode layer comprises electric conductors which are insulated from each other and are respectively and electrically connected to the corresponding connecting portions.

7. The electrostimulation apparatus of claim 6, wherein a tensile spacer is formed between each of the connecting portions and the carrier, and the carrier further has a fixing unit to fix the carrier on a part of a user.

8. The electrostimulation apparatus of claim 7, wherein the connecting portion is a conductive snap fastener, a conductive pin, and a surface of the control unit is configured to connect to the connecting portions through wires or cordless/wireless method; the power supply is a power adapter, a portable power supply, a vehicle power supply, or other power supplies which are configured to connect to the connecting portions through wires or cordless/wireless manner; the connecting portion is connected to the control unit or the power supply through a magnetic set, a set of conductive snap fastener, a flexible glue set, a pin-socket set.

9. The electrostimulation apparatus of claim 8, wherein the carrier includes a belt, a bandage, a wrap/sleeve, a guard, a pad, a grove, a sock, a shoe, a sole/insole, shorts, pants, shirts and clothes.

10. The electrostimulation apparatus of claim 1, wherein the control unit is used as a thermometer to measure temperature on the carrier and/or the user.

* * * * *